US012678554B2

(12) United States Patent
Woodman et al.

(10) Patent No.: US 12,678,554 B2
(45) Date of Patent: Jul. 14, 2026

(54) DRIP CHAMBER ASSEMBLY

(71) Applicant: CareFusion 303. Inc., San Diego, CA (US)

(72) Inventors: Huntington Woodman, Irvine, CA (US); Kelly Kloster Hon, Del Mar, CA (US); Ryan Callahan, Long Beach, CA (US); Leyla Yamin, San Diego, CA (US)

(73) Assignee: CAREFUSION 303, INC., San Diego, CA (US)

( * ) Notice: Subject to any disclaimer, the term of this patent is extended or adjusted under 35 U.S.C. 154(b) by 211 days.

(21) Appl. No.: 17/018,340

(22) Filed: Sep. 11, 2020

(65) Prior Publication Data

US 2022/0080107 A1      Mar. 17, 2022

(51) Int. Cl.
*A61M 5/14* (2006.01)

(52) U.S. Cl.
CPC ... *A61M 5/1411* (2013.01); *A61M 2005/1402* (2013.01); *A61M 2205/7518* (2013.01)

(58) Field of Classification Search
CPC ........ A61M 5/1411; A61M 2005/1402; A61M 2205/7518
See application file for complete search history.

(56) References Cited

U.S. PATENT DOCUMENTS 2,586,513 A * 2/1952 Butler .................... A61M 5/165
                                                        210/94
2,784,733 A * 3/1957 Martinez ................. A61M 5/40
                                                        137/433

3,935,111 A * 1/1976 Bentley .................. B01D 35/00
                                                        210/489
3,954,623 A * 5/1976 Hammer ............... B01D 35/00
                                                        215/261
3,978,857 A * 9/1976 McPhee ................ A61M 5/165
                                                        604/257
4,009,714 A * 3/1977 Hammer ............... A61M 5/165
                                                        604/126

(Continued)

FOREIGN PATENT DOCUMENTS

CN         101972503 A      2/2011
CN         216908806 U      7/2022

(Continued)

OTHER PUBLICATIONS

International Search Report and Written Opinion for Application No. PCT/US2021/049957, dated Dec. 21, 2021, 13 pages.

(Continued)

*Primary Examiner* — Bhisma Mehta
*Assistant Examiner* — Mark A Igel
(74) *Attorney, Agent, or Firm* — MASCHOFF BRENNAN

(57)      ABSTRACT

Drip chamber assemblies are described herein. A drip chamber assembly includes a drip chamber and a filter. The drip chamber includes a chamber body defining a chamber volume. The filter is disposed within the chamber volume. The filter includes a folded filter media, which defines an inlet portion of the chamber volume and an outlet portion of the chamber volume. The folded filter media permits inlet flow from the inlet portion of the chamber volume to the outlet portion of the chamber volume. The folded filter media captures particulate from the inlet flow.

17 Claims, 5 Drawing Sheets

(56) References Cited

U.S. PATENT DOCUMENTS

| | | | | |
|---|---|---|---|---|
| 4,073,732 A | * | 2/1978 | Lauer | B32B 5/06 |
| | | | | 55/487 |
| 4,087,363 A | * | 5/1978 | Rosemeyer | A61M 5/165 |
| | | | | 210/489 |
| 4,116,845 A | * | 9/1978 | Swank | A61M 5/165 |
| | | | | 210/451 |
| 4,126,558 A | * | 11/1978 | Luceyk | A61M 5/165 |
| | | | | 210/429 |
| 4,227,525 A | * | 10/1980 | Lundquist | B01D 19/0031 |
| | | | | 604/126 |
| 4,276,170 A | * | 6/1981 | Vaillancourt | B01D 36/001 |
| | | | | 96/6 |
| 4,303,530 A | * | 12/1981 | Shah | A61M 1/3627 |
| | | | | 210/651 |
| 4,320,001 A | * | 3/1982 | Le Boeuf | B01D 35/00 |
| | | | | 210/123 |
| 4,361,483 A | * | 11/1982 | Pall | B01D 27/005 |
| | | | | 210/451 |
| 4,450,078 A | * | 5/1984 | Walker | A61M 5/165 |
| | | | | 210/489 |
| 4,479,874 A | * | 10/1984 | Rosenberg | B01D 29/031 |
| | | | | 210/446 |
| 4,517,090 A | * | 5/1985 | Kersten | B01D 29/232 |
| | | | | 264/250 |
| 4,547,190 A | * | 10/1985 | Leason | A61M 5/165 |
| | | | | 604/185 |
| 4,690,762 A | * | 9/1987 | Katsura | B01D 19/0031 |
| | | | | 210/512.1 |
| 4,704,207 A | * | 11/1987 | Chu | B01D 29/41 |
| | | | | 210/488 |
| 4,963,262 A | * | 10/1990 | Johnstone | A47J 31/06 |
| | | | | 210/477 |
| 4,978,446 A | * | 12/1990 | Lobdell | A61M 1/0218 |
| | | | | 604/408 |
| 6,497,685 B1 | * | 12/2002 | Dennehey | B29C 45/14336 |
| | | | | 210/450 |
| 7,892,204 B2 | * | 2/2011 | Kraus | A61M 5/165 |
| | | | | 604/122 |
| 8,366,658 B2 | * | 2/2013 | Davis | A61M 39/20 |
| | | | | 604/82 |
| 10,661,215 B2 | * | 5/2020 | Williams | B01D 46/521 |
| 2002/0033370 A1 | * | 3/2002 | Bainbridge | A61M 1/303 |
| | | | | 604/6.11 |
| 2002/0162309 A1 | * | 11/2002 | Schmitz | B01D 46/2414 |
| | | | | 55/423 |
| 2006/0189937 A1 | * | 8/2006 | Miner | A61M 1/3626 |
| | | | | 604/122 |
| 2008/0209871 A1 | * | 9/2008 | German | B01D 46/2411 |
| | | | | 156/290 |
| 2014/0228806 A1 | * | 8/2014 | Alisantoso | A61M 5/1411 |
| | | | | 604/126 |
| 2015/0165351 A1 | * | 6/2015 | Lo | B01D 29/111 |
| | | | | 210/493.5 |
| 2015/0374909 A1 | * | 12/2015 | Mansour | A61M 5/1411 |
| | | | | 604/254 |
| 2018/0085695 A1 | * | 3/2018 | Wall | B01D 46/001 |
| 2021/0213197 A1 | * | 7/2021 | Urano | A61M 5/16827 |

FOREIGN PATENT DOCUMENTS

| | | | | |
|---|---|---|---|---|
| EP | 0024601 A1 | 3/1981 | | |
| JP | H4057364 A | 9/1992 | | |
| JP | 2003527934 A | 9/2003 | | |
| WO | WO-8903717 A1 | * | 5/1989 | A61M 1/3633 |

OTHER PUBLICATIONS

European Office Action for Application No. 21787182.1, dated Jan. 10, 2025, 6 pages.

Chinese Office Action for Application No. 202111044930.3, dated May 26, 2025, 16 pages including translation.

Japanese Office Action for Application No. 2023-512307, dated Jun. 3, 2025, 8 pages including translation.

Chinese Office Action for Application No. 202111044930.3, dated Oct. 31, 2025, 13 pages including translation.

Mexican Office Action for Application No. MX/a/2023/001745, dated Oct. 16, 2025, 7 pages including English translation of the requirements.

Chinese Office Action for Application No. 202111044930.3, dated Feb. 9, 2026, 10 pages including translation.

Indian Office Action for Application No. 202317017536, dated Mar. 2, 2026, 7 pages.

Japanese Decision of Rejection for Application No. 2023-512307, dated Jan. 7, 2026, 7 pages including translation.

Australian Office Action for Application No. 2021340719, dated May 11, 2026, 3 pages.

* cited by examiner

DRIP CHAMBER ASSEMBLY

FIELD OF THE INVENTION

The present disclosure generally relates to drip chambers, and in particular, to drip chambers with filters for intravenous sets.

BACKGROUND

Medical treatments often include the infusion of a medical fluid (e.g., a saline solution or a liquid medication) to patients using an intravenous (IV) catheter that is connected though an arrangement of flexible tubing and fittings, commonly referred to as an "IV set," to a source of fluid, for example, an IV bag. Prior to operation, components of the IV set can be primed with medical fluid. Further, during operation, medical fluid can be filtered to prevent the transfer of bacteria, microorganisms, and/or other pathogens. In some applications, filters can become clogged during operation.

SUMMARY

The disclosed subject matter relates to drip chamber assemblies. In certain embodiments, drip chamber assemblies are disclosed that comprise a drip chamber comprising a chamber body defining a chamber volume; and a filter disposed within the chamber volume, the filter comprising: a folded filter media, the folded filter media defining an inlet portion of the chamber volume and an outlet portion of the chamber volume, wherein the folded filter media permits inlet flow from the inlet portion of the chamber volume to the outlet portion of the chamber volume and captures particulate from the inlet flow.

In certain embodiments, a method is disclosed that comprises introducing an inlet flow into a chamber volume; permitting the inlet flow from an inlet portion of the chamber volume through a folded filter media and into an outlet portion of the chamber volume; and capturing particulate from the inlet flow in the folded filter media.

In certain embodiments, an IV set is disclosed that comprises a first portion of tubing; a second portion of tubing; and a drip chamber assembly comprising: a drip chamber comprising a chamber body defining a chamber volume, an inlet end in fluid communication with the chamber volume, and an outlet in fluid communication with the chamber volume, wherein the inlet end is coupled to the first portion of tubing and the outlet is coupled to the second portion of tubing; and a filter disposed within the chamber volume, the filter comprising: a folded filter media, the folded filter media defining an inlet portion of the chamber volume in fluid communication with the inlet end and an outlet portion of the chamber volume in fluid communication with the outlet, wherein the folded filter media permits inlet flow from the inlet portion of the chamber volume to the outlet portion of the chamber volume and captures particulate from the inlet flow.

It is understood that various configurations of the subject technology will become readily apparent to those skilled in the art from the disclosure, wherein various configurations of the subject technology are shown and described by way of illustration. As will be realized, the subject technology is capable of other and different configurations and its several details are capable of modification in various other respects, all without departing from the scope of the subject technology. Accordingly, the summary, drawings and detailed description are to be regarded as illustrative in nature and not as restrictive.

BRIEF DESCRIPTION OF THE DRAWINGS

The accompanying drawings, which are included to provide further understanding and are incorporated in and constitute a part of this specification, illustrate disclosed embodiments and together with the description serve to explain the principles of the disclosed embodiments. In the drawings.

DETAILED DESCRIPTION

The disclosed drip chamber assembly integrates a drip chamber and a filter with folded filter media. The folded filter media increases the effective filtration area of the filter, extending the life of the filter before clogging.

The detailed description set forth below is intended as a description of various configurations of the subject technology and is not intended to represent the only configurations in which the subject technology may be practiced. The detailed description includes specific details for the purpose of providing a thorough understanding of the subject technology. However, it will be apparent to those skilled in the art that the subject technology may be practiced without these specific details. In some instances, well-known structures and components are shown in block diagram form in order to avoid obscuring the concepts of the subject technology. Like components are labeled with identical element numbers for ease of understanding. Reference numbers may have letter suffixes appended to indicate separate instances of a common element while being referred to generically by the same number without a suffix letter.

While the following description is directed to drip chamber assemblies for the administration of medical fluid using the disclosed drip chamber assembly, it is to be understood that this description is only an example of usage and does not limit the scope of the claims. Various aspects of the disclosed drip chamber assembly may be used in any application where it is desirable to provide extended filter life.

The disclosed drip chamber assembly overcomes several challenges discovered with respect to certain conventional filter devices. One challenge with certain conventional filter devices is that conventional filter media can become clogged with infusate during operation. Further, another challenge with certain conventional components is that separate devices are often used for filtration and priming functionality, adding complexity to IV sets and adding to the number of tubing connections that are required in an IV set. Because certain conventional filter devices may become easily clogged or may add complexity to an IV set, the use of certain conventional filtration devices is undesirable.

Therefore, in accordance with the present disclosure, it is advantageous to provide a drip chamber assembly as described herein that allows for integration of the drip chamber and filter functionality into a single in-line component, reducing complexity and tubing connections. Further, it is advantageous to provide a drip chamber assembly that allows for extended filter life.

Examples of drip chamber assembly that allow for extended filter life and minimize complexity are now described.

Figure 1:
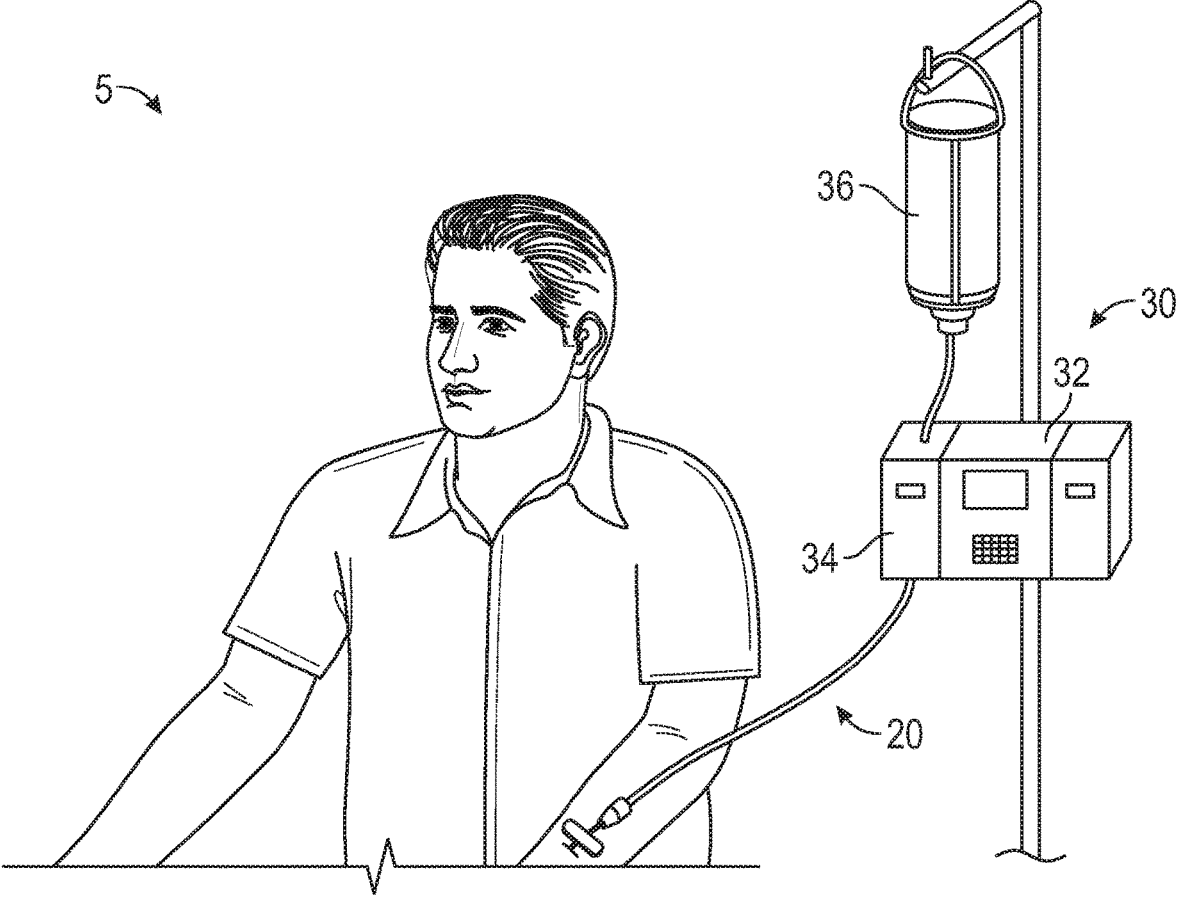
FIG. 1 depicts a patient receiving an infusion of a medical fluid using an IV pump.

FIG. 1 illustrates a patient 5 receiving an infusion of a medical fluid through an IV pump 30 according to certain aspects of the present disclosure. The IV pump 30 comprises a controller 32 and two pump modules 34. An IV set 20 is connected between a container 36 of the medical fluid and the patient 5. Prior to operation, components of the IV set 20 can be primed with medical fluid. Further, during operation, medical fluid delivered to the patient 5 can be filtered to prevent the transfer of bacteria, microorganisms, and/or other pathogens. A drip chamber assembly as described herein can allow for priming operations and filtration of the medical fluid delivered to the patient 5. In some embodiments, a drip chamber assembly can be disposed in between or in line with tubing of the IV set 20.

Figure 2:
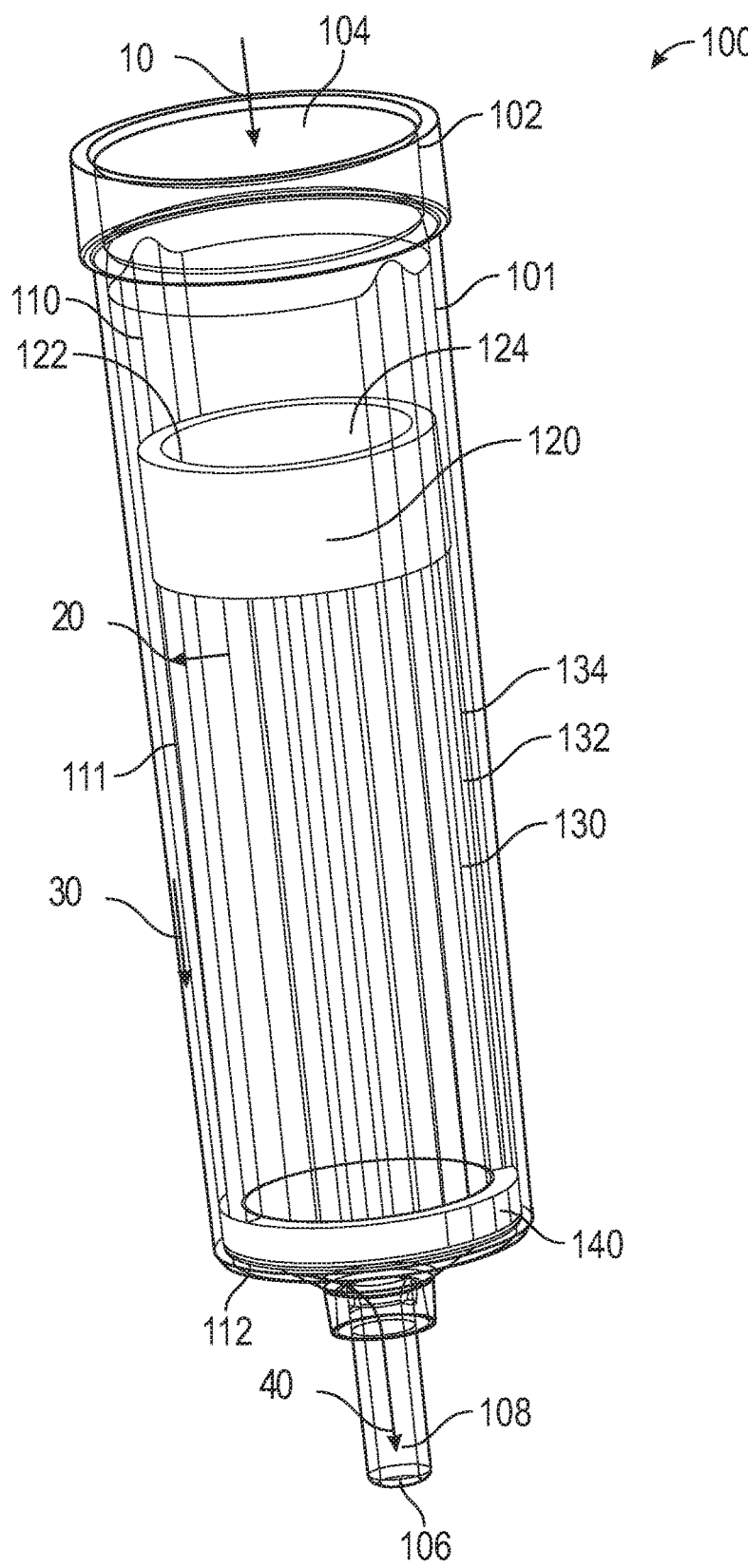
FIG. 2 illustrates a perspective view of a drip chamber assembly according to certain aspects of the present disclosure.
Figure 3:
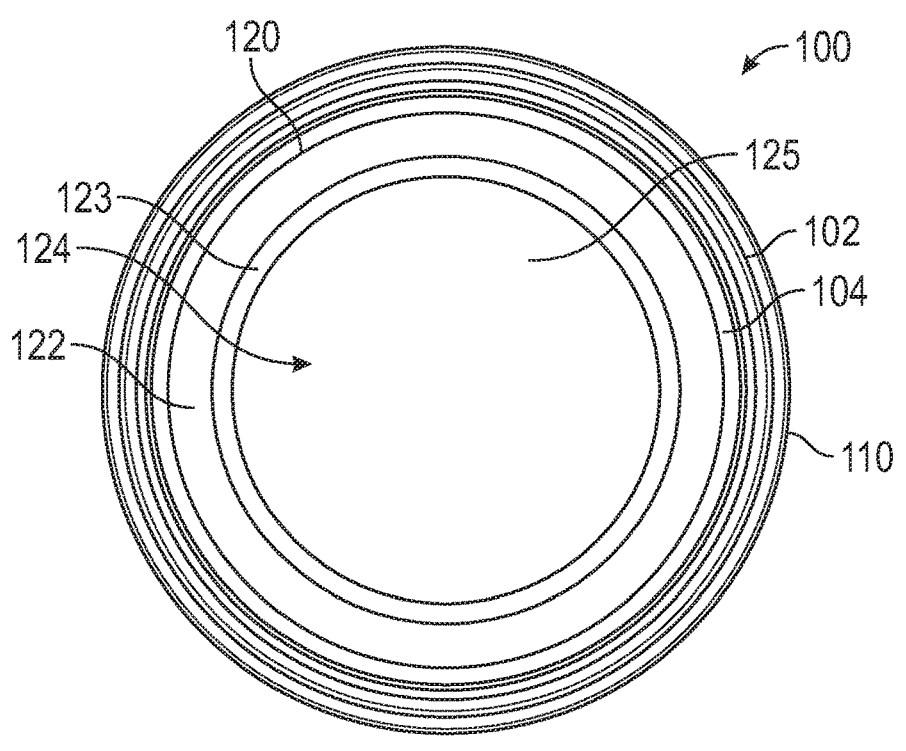
FIG. 3 illustrates a top view of the drip chamber assembly of FIG. 2.
Figure 4:
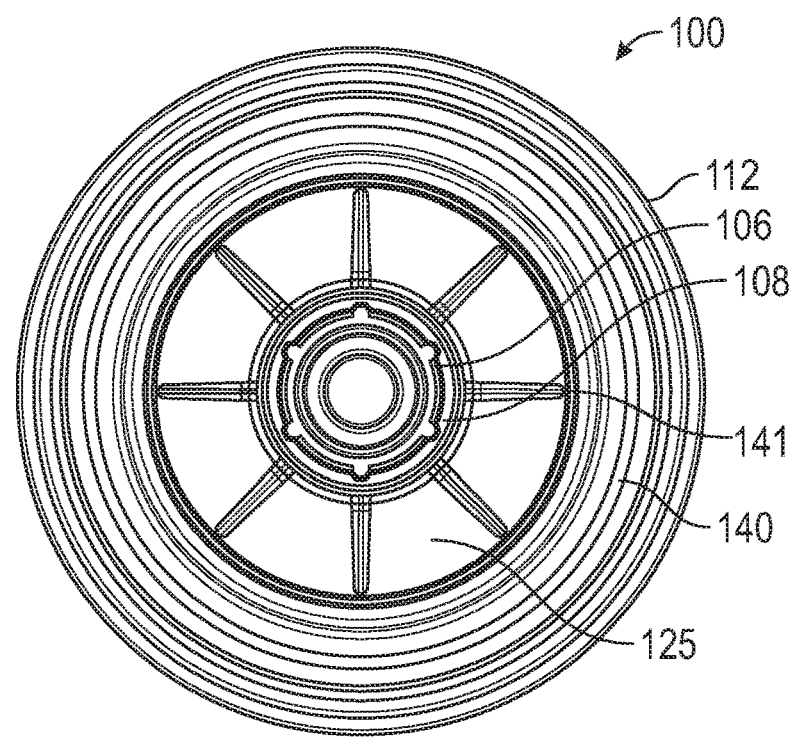
FIG. 4 illustrates a bottom view of the drip chamber assembly of FIG. 2.

FIG. 2 illustrates a perspective view of a drip chamber assembly 100 according to certain aspects of the present disclosure. FIG. 3 illustrates a top view of the drip chamber assembly 100 of FIG. 2. FIG. 4 illustrates a bottom view of the drip chamber assembly 100 of FIG. 2. In the depicted example, the drip chamber assembly 100 allows for the functionality of a drip chamber 101 while additionally allowing for filtration of medical fluid passing therethrough. As described herein, the drip chamber assembly 100 integrates a filter 120 disposed within the drip chamber 101.

Figures 5, 6:
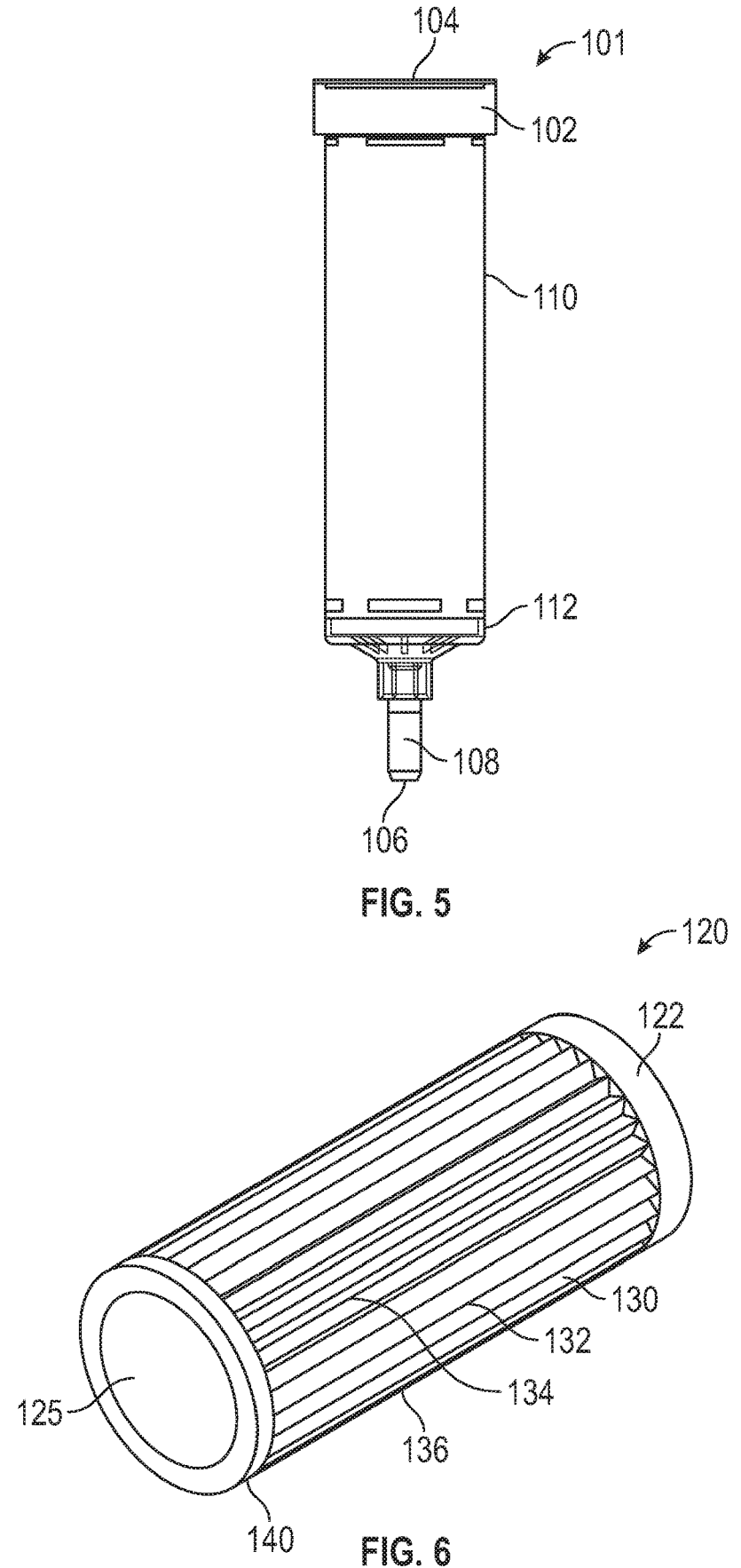
FIG. 5 illustrates a front view of a drip chamber of the drip chamber assembly of FIG. 2.
FIG. 6 illustrates a perspective view of a filter of the drip chamber assembly of FIG. 2.

FIG. 5 illustrates a front view of a drip chamber 101 of drip chamber assembly 100 of FIG. 2. With reference to FIGS. 2-5, the drip chamber 101 provides a visual indicator of the flow rate of a medical fluid therethrough. Advantageously, clinicians can monitor and adjust the flow rate of the medical fluid based on the visual indicator provided by the drip chamber 101.

During operation, medical fluid can drip or otherwise flow through the chamber volume 104 defined by the chamber body 110. Medical fluid flow 10 can enter the chamber body 110 through an upper portion or inlet portion 102 defined in the chamber body 110. Fluid flow 40 can exit the chamber body 110 through a lower portion or outlet portion 112. In some embodiments, the outlet portion 112 can include an outlet 108. The outlet lumen 106 formed in the outlet 108 can be in fluid communication with the chamber volume 104. The outlet 108 can be coupled to tubing of the IV set 20.

As fluid passes through the chamber body 110, a clinician can utilize the drip chamber 101 as a visual indicator to observe the dripping or flow of medical fluid therethrough. As can be appreciated the chamber body 110 can be transparent or semi-transparent.

In some embodiments, the chamber body 110 can equalize pressure differentials between the chamber volume 104 and the environment during operation. In some embodiments, the chamber body 110 can be formed from a resilient material to allow the chamber body 110 to be squeezed or compressed to draw in medical fluid for priming of an IV system.

In the depicted example, the drip chamber 101 can draw in medical fluid for priming of an IV system. As can be appreciated, the chamber volume 104 can be filled with a desired volume of medical fluid during the priming operation.

Figure 7:
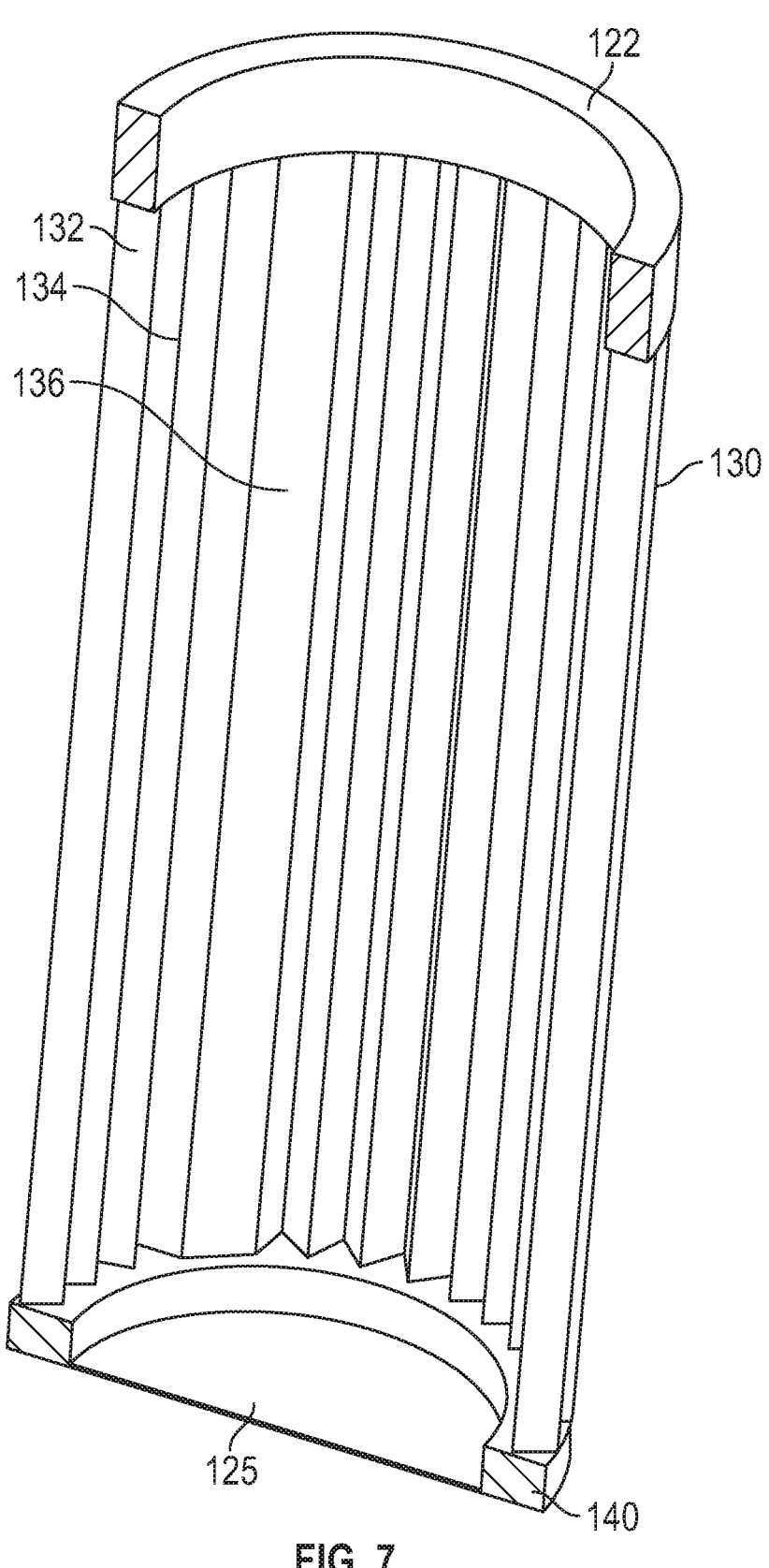
FIG. 7 illustrates a cross-sectional view of the filter of FIG. 6.

FIG. 6 illustrates a perspective view of a filter 120 of the drip chamber assembly 100 of FIG. 2. FIG. 7 illustrates a cross-sectional view of the filter 120 of FIG. 6. With reference to FIGS. 2-4, 6 and 7, during operation, as medical fluid flows through the drip chamber assembly 100, the fluid can be filtered prior to flowing out of the drip chamber 101 and into tubing of the IV set 20. In the depicted example, a filter 120 is disposed within the chamber volume 104 to filter fluid passing through the chamber volume 104.

As illustrated, fluid within the chamber volume 104 can pass through a filter 120 to prevent the transfer of bacteria, microorganisms, and/or other pathogens to the patient. During operation, fluid can flow within the chamber volume 104 to an inlet portion 124 of the chamber volume 104, through a filter media 130 to an outlet portion 111 of the chamber volume 104, as illustrated by flow arrows 20, 30, and 40. As can be appreciated, a positive pressure differential can direct fluid flow 20 from the inlet portion 124 of the chamber volume 104 through the filter media 130 to the outlet portion 111 of the chamber volume 104. Filtered fluid can flow from the outlet portion 111 through the outlet 108 of the drip chamber 101.

In the depicted example, filtered fluid can flow from the outlet portion 111 to the outlet 108 through a flow path defined between the chamber body 110 and the lower portion of the filter 120. In some embodiments, the filter 120 can be seated or spaced apart within the chamber volume 104 to define a flow path between the chamber body 110 and the lower frame 140 of the filter 120. Optionally, the lower frame 140 of the filter 120 can be disposed on raised protrusions 141 defined within the chamber body 110 can promote or otherwise define the flow path between the chamber body 110 and the lower frame 140. The raised protrusions 141 can be circumferentially disposed about a lower portion of the chamber body. The protrusions 141 can be radially spaced apart to define flow paths to the outlet portion 111.

As described herein, the filter media 130 can selectively filter the flow through the filter 120. The filter media 130 can have an average filter opening ranging between 15 to 200 microns. In some embodiments, the average filter opening can range between 180 to 200 microns. Optionally, the filter media 130 can have pores that vary in size. In some embodiments, the filter media 130 can be formed from a non-woven filter material. The filter media 130 can be formed from a resilient or expandable material. Optionally, the filter media 130 can be treated with an anti-coagulant.

Advantageously, the filter media 130 can include a plurality of pleats or folds 132 to increase the effective filtration area of the filter 120. By pleating or folding the filter media 130, the filter 120 can filter a greater amount of infusate without clogging or reducing filtration efficiency. The folds 132 in the filter media 130 can define a plurality of peaks 134 and valleys 136 along the surface of the filter 120. The radius of the bends of the peaks 134 and the valleys 136 can vary.

The filter 120 can have a generally cylindrical shape. As illustrated, the filter 120 can extend along a portion of the length of the drip chamber 101. The filter 120 can have a diameter that allows the filter 120 to fit within the chamber volume 104 of the drip chamber 101. During operation, fluid flow 20 can enter the filter 120 through an inner portion of the filter media 130 via the inlet portion 124 of the chamber volume 104. The flow 30 can move radially outward through the filter media 130 and downward into the outlet portion 111 of the chamber volume 110.

In some embodiments, the filter media 130 is supported by a filter frame. As illustrated, the filter media 130 can be supported by an upper frame 122 and/or a lower frame 140. The upper frame 122 and/or the lower frame 140 can maintain the general shape of the filter 120. Optionally, the upper frame 122 and/or the lower frame 140 can seal against the chamber body 110 to prevent flow from bypassing the filter media 130. The upper frame 122 and/or the lower frame 140 can have a generally resilient construction to maintain sealing contact with the chamber body 110 during deformation of the drip chamber 101. Further, the lower frame 140 can include an endplate 125 to prevent flow 10 and 20 from bypassing the filter media 130.

Optionally, the filter 120 is captured by features and/or geometry of the drip chamber 101. In some embodiments, the filter 120 is coupled to the drip chamber 101 via fasteners and/or an adhesive. The filter 120 may also be free floating relative to the drip chamber 101.

The present disclosure is provided to enable any person skilled in the art to practice the various aspects described herein. The disclosure provides various examples of the subject technology, and the subject technology is not limited to these examples. Various modifications to these aspects will be readily apparent to those skilled in the art, and the generic principles defined herein may be applied to other aspects.

A reference to an element in the singular is not intended to mean "one and only one" unless specifically so stated, but rather "one or more." Unless specifically stated otherwise, the term "some" refers to one or more. Pronouns in the masculine (e.g., his) include the feminine and neuter gender (e.g., her and its) and vice versa. Headings and subheadings, if any, are used for convenience only and do not limit the invention.

The word "exemplary" is used herein to mean "serving as an example or illustration." Any aspect or design described herein as "exemplary" is not necessarily to be construed as preferred or advantageous over other aspects or designs. In one aspect, various alternative configurations and operations described herein may be considered to be at least equivalent.

A phrase such as an "aspect" does not imply that such aspect is essential to the subject technology or that such aspect applies to all configurations of the subject technology. A disclosure relating to an aspect may apply to all configurations, or one or more configurations. An aspect may provide one or more examples. A phrase such as an aspect may refer to one or more aspects and vice versa. A phrase such as an "embodiment" does not imply that such embodiment is essential to the subject technology or that such embodiment applies to all configurations of the subject technology. A disclosure relating to an embodiment may apply to all embodiments, or one or more embodiments. An embodiment may provide one or more examples. A phrase such an embodiment may refer to one or more embodiments and vice versa. A phrase such as a "configuration" does not imply that such configuration is essential to the subject technology or that such configuration applies to all configurations of the subject technology. A disclosure relating to a configuration may apply to all configurations, or one or more configurations. A configuration may provide one or more examples. A phrase such a configuration may refer to one or more configurations and vice versa.

In one aspect, unless otherwise stated, all measurements, values, ratings, positions, magnitudes, sizes, and other specifications that are set forth in this specification, including in the claims that follow, are approximate, not exact. In one aspect, they are intended to have a reasonable range that is consistent with the functions to which they relate and with what is customary in the art to which they pertain.

In one aspect, the term "coupled" or the like may refer to being directly coupled. In another aspect, the term "coupled" or the like may refer to being indirectly coupled.

Terms such as "top," "bottom," "front," "rear" and the like if used in this disclosure should be understood as referring to an arbitrary frame of reference, rather than to the ordinary gravitational frame of reference. Thus, a top surface, a bottom surface, a front surface, and a rear surface may extend upwardly, downwardly, diagonally, or horizontally in a gravitational frame of reference.

Various items may be arranged differently (e.g., arranged in a different order, or partitioned in a different way) all without departing from the scope of the subject technology. All structural and functional equivalents to the elements of the various aspects described throughout this disclosure that are known or later come to be known to those of ordinary skill in the art are expressly incorporated herein by reference and are intended to be encompassed by the claims. Moreover, nothing disclosed herein is intended to be dedicated to the public regardless of whether such disclosure is explicitly recited in the claims. No claim element is to be construed under the provisions of 35 U.S.C. § 112, sixth paragraph, unless the element is expressly recited using the phrase "means for" or, in the case of a method claim, the element is recited using the phrase "step for." Furthermore, to the extent that the term "include," "have," or the like is used, such term is intended to be inclusive in a manner similar to the term "comprise" as "comprise" is interpreted when employed as a transitional word in a claim.

The Title, Background, Summary, Brief Description of the Drawings and Abstract of the disclosure are hereby incorporated into the disclosure and are provided as illustrative examples of the disclosure, not as restrictive descriptions. It is submitted with the understanding that they will not be used to limit the scope or meaning of the claims. In addition, in the Detailed Description, it can be seen that the description provides illustrative examples and the various features are grouped together in various embodiments for the purpose of streamlining the disclosure. This method of disclosure is not to be interpreted as reflecting an intention that the claimed subject matter requires more features than are expressly recited in each claim. Rather, as the following claims reflect, inventive subject matter lies in less than all features of a single disclosed configuration or operation. The following claims are hereby incorporated into the Detailed Description, with each claim standing on its own as a separately claimed subject matter.

The claims are not intended to be limited to the aspects described herein, but is to be accorded the full scope consistent with the language claims and to encompass all legal equivalents. Notwithstanding, none of the claims are intended to embrace subject matter that fails to satisfy the requirement of 35 U.S.C. § 101, 102, or 103, nor should they be interpreted in such a way.

What is claimed is:

1. A drip chamber assembly, comprising:
   a drip chamber comprising a chamber body defining a chamber volume, wherein the chamber body is deformable;
   a filter disposed within the chamber volume and free floating relative to the drip chamber, the filter comprising:

a folded filter media, the folded filter media defining an inlet portion of the chamber volume and an outlet portion of the chamber volume, wherein the outlet portion of the chamber volume is formed between the folded filter media and the chamber body, the folded filter media permits inlet flow from the inlet portion of the chamber volume to move radially outward to the outlet portion of the chamber volume and captures particulate from the inlet flow; and a frame to support the folded filter media, the frame comprising:

an upper portion of the frame comprising a first continuous sealing exterior circumferential surface that seals against the chamber body to direct the inlet flow to a radially inner portion of the folded filter media; and a lower portion of the frame, wherein the lower portion of the frame is configured to resiliently deform with the chamber body, and a flow path from the outlet portion of the chamber volume to an outlet is formed between the chamber body and the lower portion of the frame.

2. The drip chamber assembly of claim 1, wherein the folded filter media defines a plurality of peaks and valleys between the inlet portion of the chamber volume and the outlet portion of the chamber volume.

3. The drip chamber assembly of claim 1, wherein the folded filter media has a pore size between 15 to 200 microns.

4. The drip chamber assembly of claim 3, wherein the pore size is between 180 to 200 microns.

5. The drip chamber assembly of claim 1, wherein the folded filter media comprises an anti-coagulant treatment.

6. The drip chamber assembly of claim 1, wherein the chamber volume is in fluid communication with the inlet portion of the chamber volume.

7. The drip chamber assembly of claim 1, wherein the folded filter media surrounds the inlet portion of the chamber volume.

8. The drip chamber assembly of claim 1, wherein the filter is coupled to the drip chamber.

9. The drip chamber assembly of claim 1, the chamber body defining an inlet end in fluid communication with the inlet portion of the chamber volume.

10. The drip chamber assembly of claim 1, the chamber body defining the outlet in fluid communication with the outlet portion of the chamber volume.

11. The drip chamber assembly of claim 1, wherein the lower portion of the frame is positioned on raised protrusions of the chamber body.

12. A method, comprising:

introducing an inlet flow into a chamber volume defined by a chamber body;

providing a filter within the chamber volume, wherein the filter is free floating relative to the chamber body, the filter comprising a folded filter media; supporting the folded filter media within the chamber volume via a frame;

sealing a first continuous sealing exterior circumferential surface of an upper portion of the frame against the chamber body to direct the inlet flow from an inlet portion of the chamber volume to a radially inner portion of the folded filter media, radially outward through the folded filter media, and into an outlet portion of the chamber volume defined between the folded filter media and the chamber body;

capturing particulate from the inlet flow in the folded filter media as the inlet flow moves radially outward from the inlet portion to the outlet portion of the chamber volume;

resiliently deforming the chamber body; and resiliently deforming a lower portion of the frame as the chamber body is deformed.

13. The method of claim 12, wherein the inlet portion of the chamber volume is surrounded by the folded filter media.

14. The method of claim 12, further comprising:

directing flow from the outlet portion of the chamber volume into an outlet in fluid communication with the chamber volume.

15. The method of claim 12, wherein supporting the folded filter media within the chamber volume further comprises positioning the lower portion of the frame on raised protrusions of the chamber body.

16. An IV set comprising:

a first portion of tubing;

a second portion of tubing; and a drip chamber assembly comprising:

a drip chamber comprising a chamber body defining a chamber volume, an inlet end in fluid communication with the chamber volume, and an outlet in fluid communication with the chamber volume, wherein the inlet end is coupled to the first portion of tubing and the outlet is coupled to the second portion of tubing and the chamber body is deformable;

a filter disposed within the chamber volume and free floating relative to the drip chamber, the filter comprising:

a folded filter media, the folded filter media defining an inlet portion of the chamber volume in fluid communication with the inlet end and an outlet portion of the chamber volume in fluid communication with the outlet, wherein the outlet portion of the chamber volume is formed between the folded filter media and the chamber body, the folded filter media permits inlet flow from the inlet portion of the chamber volume to move radially outward to the outlet portion of the chamber volume and captures particulate from the inlet flow; and a frame to support the folded filter media, the frame comprising:

an upper portion of the frame comprising a first continuous sealing exterior circumferential surface of that seals against the chamber body to direct the inlet flow to a radially inner portion of the folded filter media; and a lower portion of the frame, wherein the lower portion of the frame is configured to resiliently deform with the chamber body.

17. The IV set of claim 16, wherein the lower portion of the frame is positioned on raised protrusions of the chamber body.

* * * * *